(12) United States Patent
Videen (10) Patent No.: US 6,963,400 B1
(45) Date of Patent: Nov. 8, 2005

(54) SYSTEMS AND METHODS FOR ANALYZING PARTICLE SYSTEMS USING POLARIZED SCATTERED LIGHT

(75) Inventor: Gorden Videen, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 212 days.

(21) Appl. No.: 10/642,676

(22) Filed: Aug. 19, 2003

(51) Int. Cl.$^7$ .............................. G01H 21/00; G01J 4/00
(52) U.S. Cl. ....................... 356/338; 356/364; 356/438
(58) Field of Search ................................. 356/337, 338, 356/340, 342, 364, 438, 439, 441, 442

(56) References Cited

U.S. PATENT DOCUMENTS

| | | | | |
|---|---|---|---|---|
| 4,492,467 | A | * | 1/1985 | Drain et al. ................. 356/336 |
| 4,770,529 | A | | 9/1988 | Levinson et al. ............ 356/153 |
| 5,028,119 | A | | 7/1991 | Hegg et al. .................. 350/174 |
| 5,060,063 | A | | 10/1991 | Freeman ...................... 358/101 |
| 6,052,187 | A | | 4/2000 | Krishnan et al. ............ 356/364 |
| 6,097,488 | A | | 8/2000 | Grek et al. .................. 356/364 |
| 6,124,928 | A | | 9/2000 | Slater .......................... 356/317 |
| 6,138,083 | A | | 10/2000 | Videen ........................ 702/155 |
| 6,163,408 | A | | 12/2000 | Larussa ....................... 359/630 |
| 6,239,873 | B1 | | 5/2001 | Videen ........................ 356/369 |
| 6,411,441 | B1 | | 6/2002 | Videen ........................ 359/631 |
| 6,414,797 | B1 | | 7/2002 | Videen ........................ 359/631 |

OTHER PUBLICATIONS

Patent Application filed Nov. 6, 2000, assigned U.S. Appl. No. 09/707,291 and entitled Wide-Angle Backscatter Probe Having a Rotatable Beamsplitter and Method of Measuring with Same.

Yu. G. Shkuratov, M.A. Kreslavsky, A.A Ovcharenko, D.G Stankevich, and E.S Zubko; Opposition Effects from Clementine Data and Mechanisms of Backscatter; 1999; pp. 132-155.

Vera K. Rosenbush, Viktor V. Avramchuk, and Aleksandr E. Rosenbush; Polarization Properties of the Galilean Satellites of Jupiter: Observations and Preliminary Analysis; Sep. 20, 1977; pp. 402-414.

Karri Muinonen; Coherent Backscattering by Solar System Dust Particles; 1993; pp. 271-296.

Yu. Shkuratov, A. Ovcharenko, and E. Zubko, O. Miloslavskaya, K. Muinonen, J. Piironen, R. Nelson, W. Smythe, V. Rosenbush, and P. Helfenstein; The Opposition Effect and Negative Polarization of Structural Analogs for Planetary Regoliths; 2002; pp. 396-416.

Michael I. Mishchenko; On the Nature of the Polarization Opposition Effect Exhibited by Saturn's Rings; The Astrophysical Journal; Jul. 1, 1993; pp. 351-361.

M. I. Mishchenko; Polarization Effects in Weak Localization of Light: Calculation of the Copolarized and Depolarized Backscattering Ehancement Factors; Physical Review B; Dec. 1991; pp. 597-600.

(Continued)

*Primary Examiner*—Gregory J. Toatley, Jr.
*Assistant Examiner*—Roy M. Punnoose
(74) *Attorney, Agent, or Firm*—William Randolph (57) ABSTRACT

Methods for analyzing particle systems using polarized scattered light are provided. An exemplary method comprises the steps of: providing models of multiple arbitrary particle systems; performing ray-trace analysis with respect to the models over a range of scatter angles, the ray-trace analysis involving only use of second-order rays; receiving information corresponding to a particle system of interest; and predicting at least one characteristic of the particle system of interest using information generated during the ray-trace analysis. Systems and other methods are provided.

20 Claims, 6 Drawing Sheets

OTHER PUBLICATIONS

M. I. Mishchenko; Enhanced Backscattering of Polarized Light from Discrete Random Media: Calculationsin in Exactly the Backscattering Direction; J. Opt. Soc. Am. A/vol. 9, No. 6/ Jun. 1992; pp. 978-982.

M. I. Mishchenko, Jean-Marc Luck, and Theo M. Nieuwenhuizen; Full Angular Profile of the Coherent Polarization Opposition Effect; J. Opt. Soc. Am. A/vol. 17, No. 5/May, 2000; pp. 888-891.

Ismo V. Lindell, Ari H. Sihvolva, Karri O. Muinonen, and Peter W. Bardber; Scattering By a Small Object to an interface; J. Opt. Soc. Am. A/vol. 8, No. 3/Mar. 1991; pp. 472-476.

K. O. Muinonen; A.H. Sihvola; I.V. Lindell; and K.A. Lumme; Scattering by a Small Object Close to An Interface; J. Opt. Soc. Am. A/vol.8, No.3/Mar. 1991; pp. 477-482.

Karri Muinonen; Coherent Backscattering by Absorbing and Scattering Media; Sixth Conference on Light Scattering by Nonspherical Particles; pp. 233-226.

J.E. Geak and M. Geake; A Remote-Sensing Method for Sub-Wavelength Grains on Planetary Surfaces by Optical Polarimetry; Mon. Nat. R. astr. Soc. (1990) 46-55.

Milo Wolff; Polarization of Light Reflected from Rough Planetary Surface; Applied Optics; Jun., 1975; pp. 1395-1405.

K. Muinonen, M Kokko, S. Pohjolainen; and P. Hakala; Proceedings of the Finnish Astronomical Society; Observatory and Astrophysics Laboratory, University of Helsinki; 1990; pp. 12-15.

Nadia T. Zakharova and Michael I. Mishchenko; Scattering Properties of Needlelike and Platelike Ice Spheriods With Moderate Sized Parameters; Applied Optics/vol. 39, No. 27/ Sep. 20, 2000; pp. 5052-5057.

* cited by examiner

SYSTEMS AND METHODS FOR ANALYZING PARTICLE SYSTEMS USING POLARIZED SCATTERED LIGHT

GOVERNMENT INTEREST

The invention described herein may be manufactured, used, and licensed by or for the United States Government.

BACKGROUND

1. Technical Field

The disclosure relates to particle system analysis. More specifically, the disclosure relates to systems and methods that involve the use of polarization characteristics of light for analyzing particle systems.

2. Description of the Related Art

The polarization state of light is often described in relation to a plane of incidence defined by the vectors drawn in the direction of the incident and scattered rays. The transverse electric (TE) polarization refers to the polarization state of the light whose electric field vectors oscillate transverse, or perpendicular to this plane of incidence. The transverse magnetic (TM) polarization refers to the polarization state of the light whose magnetic field vectors oscillate transverse, or perpendicular to this plane of incidence. When a complex particle system having no preferentially oriented structure is illuminated by unpolarized light, the polarization state of the scattered light in the near-backward direction may be biased in favor of the TM state. Because fundamental physical processes like dipole scattering and Fresnel reflections favor the TE polarization state, this state is perhaps more commonly seen. A dipole may be described as a sphere whose total dimension is much smaller than the wavelength $\lambda$ of the incident light. A bias toward the TM state is referred to as a negative polarization, and this negative polarization in the near-backward-scatter (~<10 degrees from exact back-scatter) is sometimes referred to as the "Polarization Opposition Effect" (POE). On the basis of symmetry considerations, we expect the polarization in the exact back-scatter direction to be zero.

There appears to be two branches to the POE. One branch manifests itself as an asymmetric dip in the linear polarization state at approximately or less than 1 degree from the exact back-scatter direction. Researchers observing astronomical bodies have observed that the minimum position of this branch is approximately the width of the photometric opposition effect, i.e., the peak in the total intensity in the exact back-scatter direction produced by the coherent back-scattering mechanism, as described by V. K. Resonebush, V. V. Avramchuk, A. E. Rosenbush, and M. I. Mishchenko, "Polarization properties of the Galilean satellites of Jupiter: observations and preliminary analysis," Astrophys. J. 487, 402–414 (1997), which is incorporated by reference herein. The photometric opposition effect refers to an increase in the absolute intensity of the scattered light in the backscattered direction and the maximum of this increase is located in the exact backward-scattering direction.

Another branch appears to be symmetric and parabolically shaped and is located at larger scattering angles, approximately but not limited to 5°–20° from the exact backward-scattering direction. It has been observed that one or both of these negative polarizations may be present in the same scattering system. As used herein, both branches of negative polarization phenomena are referred to as the polarization opposition effect (POE). Additional background information on the POE is provided, for example, by Muinonen, Shkuratov, et al., and the references cited therein. K. Muinonen, "Coherent back-scattering by solar system dust particles," in Asteroids, Comets and Meteors, A. Milani, M. Di Martino, and A. Cellino, eds. (Kluwer, Dordrecth, the Netherlands 1974), pp. 271–296; Yu Shkruatov, A. Ovcharenko E. Zubko, V. Kaydash, D. Stankevich, V. Omelchenko, O. Miloslavskaya, K. Muinonen, J. Piironen, S. Kaasalaienen, R. Nelson, W. Smythe, V. Rosenbush and P. Helfenstein, "The opposition effect and negative polarization of structural analogs of planetary regoliths," Icarus 159, 396–416 (2002), each of which is incorporated herein by reference.

The asymmetric branch of the POE has been inextricably linked with other phenomena, such as coherent back-scattering enhancement. See, M. I. Mishchekno, "On the nature of the polarization opposition effect exhibited by Saturn's rings," Astrophys. J. 411, 351–361 (1993), which is incorporated herein by reference.

When a light ray traverses through a random medium to a detector, it is accompanied by another ray striking all the elements of the system in reverse order. When the detector is in the exact back-scatter direction, these rays constructively interfere because they have traversed the same path length but in reverse directions. When the detector is not in the exact back-scatter direction, the path lengths of these two reciprocal rays are no longer identical, and we see the intensity drop off because the constructive interference condition is optimized. The width of this peak is inversely proportional to the difference in path length between these two rays.

In a flourish of research along parallel lines, various researchers were able to show that the coherent back-scatter mechanism was also responsible for the asymmetric branch of the POE. Earlier approaches considered rigorous methods applicable to specific scattering systems, such as use of the vector theory of coherent back-scattering for a semi-infinite medium of the Rayleigh particles, V. D. Ozrin, "Exact solution for the coherent back-scattering of polarized light from a random medium of Rayleigh scatterers," M. I. Mishchenko, "Polarization effects in weak localization of light: calculation of the copolarized and depolarized backscattering enhancement factors," Phys. Rev. B 44, 12579–12600 (1991); M. I. Mishchenko, "Enhanced backscattering of polarized light from discrete random media," J. Opt. Soc. Am. A 9, 978–982 (1992); M. I. Mishchenko, J. J. Luck and T. M. Nieuwenhuizen (hereinafter Mishchenko et. al.), "Full angular profile of the coherent polarization opposition effect," J. Opt. Soc. Am. A 17, 888–891, (2000) or scattering from small particles near a surface, I. V. Lindell, A. H. Sihovla, K. O. Muinonen, and P. W. Barber, "Scattering by a small object close to an interface. I. Exact image theory formulation," J. Opt. Soc. Am. A 8, 472–476 (1991) K. O. Muinonen, A. H. Sihvola, I. V. Lindell, and K. A. Lumme, "Scattering by a small object close to an interface. I. Study of back-scattering," J. Opt. Soc. Am. A 8, 477–482 (1991), each of which is incorporated by reference herein.

More recent approaches applied Monte-Carlo-type raytracing computations for a generated particle system, involved keeping track of the phase of the scattered rays (K. Muinonen, "Coherent back-scattering by absorbing and scattering media," in Light Scattering by Nonshperical Particles, B. Gustafson, L. Kolokolova, and G. Videen, eds. (U.S. Army Research Laboratory, Adelphi, Md., 2002) 223–226, which is incorporated herein reference herein) or involved an approximate expression for the scattering by a population of scatters. See, Yu. Shkuratov, M. Kreslavsky, A. Ovcharenko, D. Stankevich, E. Zubko, C. Pieters, and G.

Arnold, "Opposition effect from Clementine data and mechanisms of back-scatter," Icarus 141, 132–155 (1999), which is also incorporated by reference herein. Although these methods are significantly different in approach, there are significant similarities in their results. Part of the reason for this is that the polarization state of light scattered from a Rayleigh particle and from a surface facet are similar.

Because the two branches of the POE have significantly different shapes and one or both may be present in a scattering system, there is some debate as to the underlying physical mechanism of the symmetric, parabolically shaped branch. This was the subject of several discussions at a North Atlantic Treaty Organization Advance Research Workshop on the "Optics of Cosmic Dust" held in Bratislava, Slovakia, 16–19 Nov. 2001. Some researchers argued that the coherent back-scatter mechanism can explain the observations of both asymmetric and symmetric branches of the POE, whereas others did not believe that the evidence as yet presented provides an adequate proof of the mechanism. It appears that the source of some of the confusion is that, in the calculations of Mishchenko, et al., the POEs for a population of Rayleigh scatterers have the same asymmetric shape regardless of the mean free path. In fact, the polarization is even plotted as a function of a dimensionless parameter $q=kl\gamma$, where l is the mean free path (or average distance a ray will travel before interacting with another surface dipole), k is the spatial frequency defined in terms of wavelength $\lambda$ as $k=2\pi/\lambda$, and $\gamma$ is the scattering angle; hence the angular minimum can be found directly from this plot as $$q_{min} \approx \frac{1.68}{kl}.$$

Other methodologies that are able to produce a more symmetric, parabolic branch at larger scattering angles are either approximate techniques or ones in which the physical mechanisms are not as transparent. The presence of sometimes one and sometimes both branches measured from the same object has served to add to the confusion. Adding fuel to the fire is the experimental research of Geake and Geake; J. E. Geake and M. Geake, "A remote-sensing method for sub-wavelength grains on planetary surfaces by optical polarimetry," Mon. Notes R. Astron. Soc. 245, 46–55 (1990), which is incorporated herein by reference. They discovered that the angular minimal positions measured from the back-scatter of their samples increase with particle size parameter. This is exactly the opposite of what would be predicted by a coherent back-scatter mechanism. Much of the current understanding of the POE is contained in four chapters (astronomical observations, laboratory measurements, theory, and numerical techniques) of a book written by participants of the aforementioned workshop; specifically, G. Videen and M. Kocifaj, eds., "Optics of Cosmic Dust" (Kluwer Academic, Dordrecht, The Netherlands, 2002), which is incorporated by reference herein.

SUMMARY

Systems and methods for analyzing particle systems using polarized scattered light are provided. In this regard, an embodiment of a method comprises the steps of: providing models of multiple arbitrary particle systems; performing ray-trace analysis with respect to the models over a range of scatter angles, the ray-trace analysis involving only use of second-order rays; receiving information corresponding to a particle system of interest; and predicting at least one characteristic of the particle system of interest using information generated during the ray-trace analysis.

Another embodiment of a method comprises the steps of: calculating relationships between polarization states and back-scatter angles with respect to multiple arbitrary particle systems; receiving information corresponding to a particle system of interest; correlating the information received with the relationships calculated to determine a best fit based, at least in part, on a minimum value of the polarization state of the particle system of interest; and using the best fit to estimate at least one characteristic of the particle system of interest.

An embodiment of a system for analyzing a particle system using polarized scattered light comprises: a model of multiple dipole particle systems and a computer operative to access the model. The model is configured to provide information corresponding to polarization state and back-scatter angle of the multiple dipole particle systems at multiple separation parameters (l) using second-order ray-trace analysis. The computer is further operative to: receive information corresponding to a particle system of interest; and predict at least one characteristic of the particle system of interest using the information provided by the model.

An embodiment of a computer-readable medium has a computer program stored thereon. The computer program is executable to perform computer-implemented method steps, the method steps comprising: receiving information corresponding to a model of a distributed system of dipoles; generating information corresponding to polarization state and back-scatter angle of the model at multiple separation parameters (l) using second-order ray-trace analysis; receiving information corresponding to a particle system of interest; and predicting at least one characteristic of the particle system of interest using the information generated.

Another embodiment of a computer-readable medium has a computer program stored thereon for performing the computer-implemented method steps of: calculating relationships between polarization states and back-scatter angles with respect to multiple arbitrary particle systems; receiving information corresponding to a particle system of interest; correlating the information received with the relationships calculated to determine a best fit based, at least in part, on a minimum value of the polarization state of the particle system of interest; and using the best fit to estimate at least one characteristic of the particle system of interest.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

As will be described in detail here, systems and methods for analyzing particle systems involve the use of second-order ray-tracing models of the light scattered by a cloud of randomly positioned dipoles. In particular, in some embodiments, only the second-order effects are considered.

Modeling the scatter from a population of dipoles has shown that the shape of the POE does not change, remaining asymmetric regardless of the minima position; in fact, the polarization only depends on a dimensionless parameter $q=kl\gamma$, where l is the mean free path and $\gamma$ is the scattering angle measured from the exact back-scatter direction. Ray-tracing calculations, however, show that the shape of the POE changes and becomes symmetric when l decreases. Whether this is an artifact of the approximations in the calculations or whether this is the physical behavior has yet to be resolved.

Recently a slightly different approach to the ray-tracing solution has been taken in which a statistical representation of a particle system composed of surface facets was used. As might be expected the method qualitatively reproduces the results of the ray-tracing analyses in which the POE becomes symmetric when the mean free path l decreased. One particular advantage to this latter approach is that the physics is greatly simplified: only second-order rays are considered (that is, rays that encounter and are scattered by exactly two dipoles); and Fresnel reflections and coherent interference of reciprocal rays are the only two physical mechanisms present in the model. The approach is similar to the more rigorous analysis of Muinonen, K., "Electromagnetic scattering by two interacting dipoles", Proceedings of the 1989 URSI EM Theory Symposium, pages 428–430, who examined the scattered fields from a system of two dipoles and integrated the resulting intensities over all orientations. In this analysis, only the second-order contributions, i.e., the rays which interact with exactly two dipoles before proceeding to the detector, are considered. We also include the constructive interference between reciprocal rays, i.e., those which contribute to coherent back-scatter.

Figure 1:
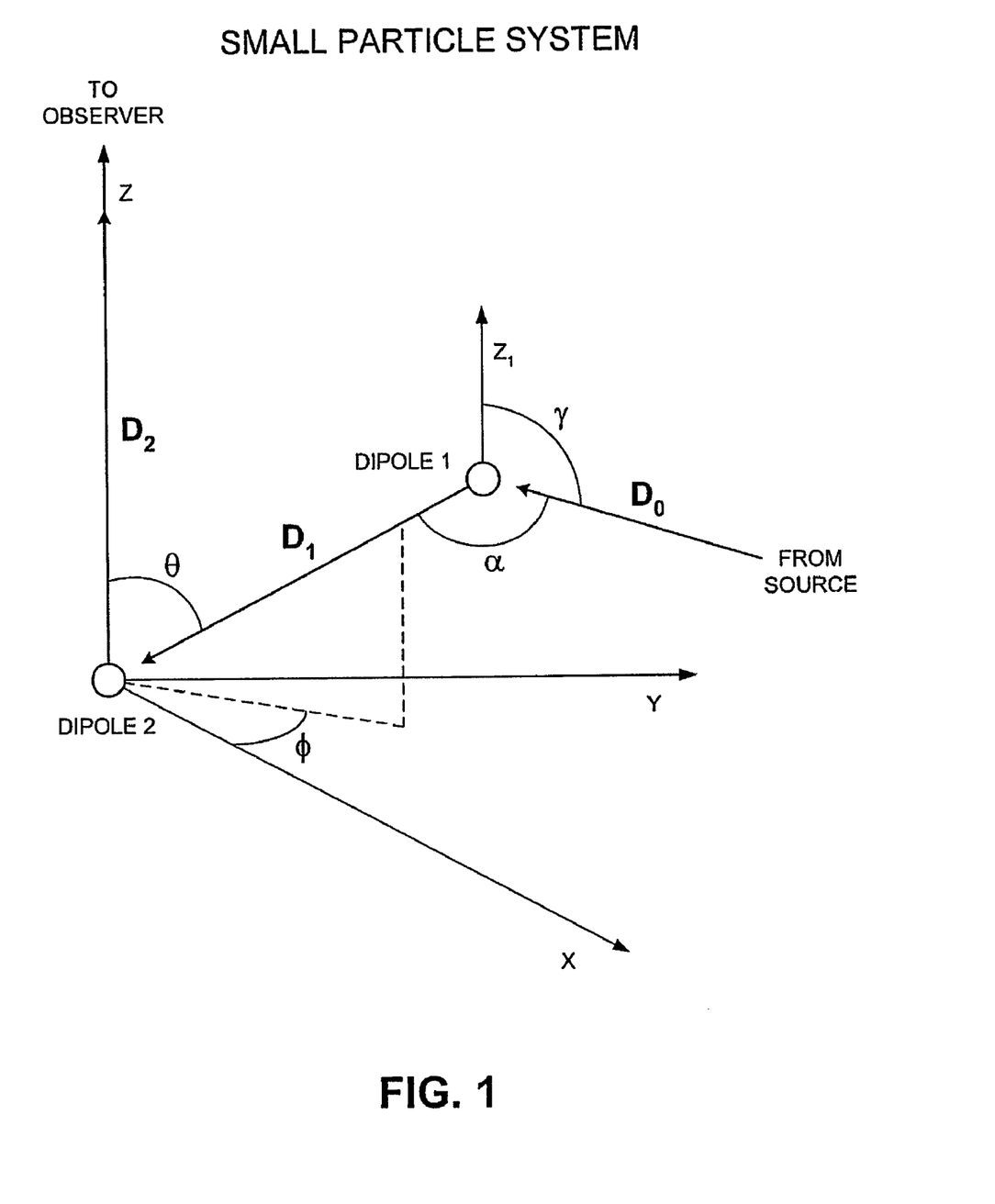
FIG. 1 is a schematic diagram depicting geometry of a representative small particle system.

A diagram of the scattering geometry used in the model is shown in FIG. 1. A light ray traveling in a plane parallel to the x-z plane, oriented at angle $\gamma$ from the z axis, strikes Dipole 1 located at the point (r, θ, ø). This ray travels in the direction of vector $D_0$. After being scattered by Dipole 1, the ray, traveling in the direction of vector $D_1$, continues to Dipole 2. Dipole D2 is located at the origin, and scatters the ray in a direction parallel to the positive z axis, given by $D_2$, to the observer, e.g., a detector. The relevant unit ray vectors in Cartesian coordinates are given by $$D_0=(\sin\gamma,0,-\cos\gamma)$$

$$D_1=(-\sin\theta\cos\phi, -\sin\theta\cos\phi, -\cos\theta)$$

$$D_2=(0,0,1) \quad (1)$$

The scattering angle from Dipole 1 is given by $$\alpha=\pi-\arccos(-\sin\theta\cos\phi\sin\gamma+\cos\theta\cos\gamma). \quad (2)$$

The scattering planes are different for each dipole and must be taken into account. The orientation of the scattering plane of Dipole 1 with respect to Dipole 2 is designated $\theta_{12}$ and is given by $$\cos\theta_{12}=\frac{\sin\theta\cos\gamma+\cos\theta\cos\phi\sin\gamma}{\sqrt{\sin^2\theta\sin^2\phi+(\sin\theta\cos\phi\cos\gamma+\cos\theta\sin\gamma)^2}}. \quad (3)$$

The last orientation of the scattering plane of Dipole 2 with respect to the entire scattering system is designated by $\phi$. We consider the polarization states of the detected light separately.

We assume that the light from the source is unpolarized. The electric fields of light scattered to the observer can be expressed as $$\begin{pmatrix}E_s\\E_p\end{pmatrix}\sim\begin{pmatrix}\cos\phi & \sin\phi\\-\sin\phi & \cos\phi\end{pmatrix}\begin{pmatrix}1 & 0\\0 & \cos(\pi-\theta)\end{pmatrix}\begin{pmatrix}\cos\theta_{12} & \sin\theta_{12}\\-\sin\theta_{12} & \cos\theta_{12}\end{pmatrix}\begin{pmatrix}E_0\\\cos(\pi-\alpha_{01})E_0\end{pmatrix}. \quad (4)$$

Note that this expression contains two scattering amplitude matrices from the dipoles and two system rotations. The S and P polarization states are standard scientific notations: the s-polarization state is identified with the TE polarization state and the p-polarization state is identified with the TM polarization state. The s and p subscripts on the electric field amplitudes and intensities refer to the components of these particular states. We proceed by expressing the intensities and then incorporating the coherent back-scattering factors in these expressions. For a cloud of dipole scatterers, it is necessary to know the density of dipoles and their extinction cross-sections. In this analysis, we are only concerned with the mean free path l of a ray through the system. By assuming Beer's law, we can express the probability density of a ray traversing through the system as $P_x=\exp(-x/l)$. The total intensity is proportional to the integrated intensity from all orientations of dipole pairs:

$$\begin{pmatrix}I_s\\I_p\end{pmatrix}\sim\iiint\begin{pmatrix}E_s^*E_s\\E_p^*E_p\end{pmatrix}_{11}\exp(-\chi/l)\sin\theta\,d\theta\,d\phi\,d\chi. \quad (5)$$

We incorporate the interference of reciprocal rays by considering the fields in Eqn. 5 to be the superposition of the reciprocal rays:

$$E_s=E_s^{(1)}+E_s^{(2)};\quad E_p=E_p^{(1)}+E_p^{(2)}; \quad (6)$$

where $E_s^{(1)}$ is the complex amplitude of the ray from the source that strikes Dipole 1, then Dipole 2 before traveling to the observer, and $E_s^{(2)}$ is the complex amplitude of the ray from the source that strikes Dipole 2, then Dipole 1 before going to the observer, and likewise for the p-component. The electric field components now vary from each other by a phase difference $\exp(i\Phi)$ and then Eqn. 6 can now be written as $$E_s^* E_s = 2E_s^{(1)*} E_s^{(1)} (1+\cos\Phi); E_p^* E_p = 2 E_p^{(1)*} E_p^{(1)} (1+\cos\Phi) \quad (7)$$

$$\Phi = k|D_1|(-\cos\theta + \sin\gamma\sin\theta\cos\phi + \cos\gamma\cos\theta) \quad (8)$$
$$= \alpha|D_1|.$$

Integrating Eqn. 5 over the separation distance x between the dipoles now yields $$\begin{pmatrix} I_s \\ I_p \end{pmatrix} \sim 2 \int\int \begin{pmatrix} E_s^{(1)} * E_s^{(1)} \\ E_p^{(1)} * E_p^{(1)} \end{pmatrix} \begin{pmatrix} 2 + l^2\alpha^2 \\ 1 + l^2\alpha^2 \end{pmatrix} \sin\theta \, d\theta \, d\phi. \quad (9)$$

Equation 9 provides a second-order ray-tracing solution of the s and p polarization intensities scattered by a cloud of dipoles.

Figure 2:
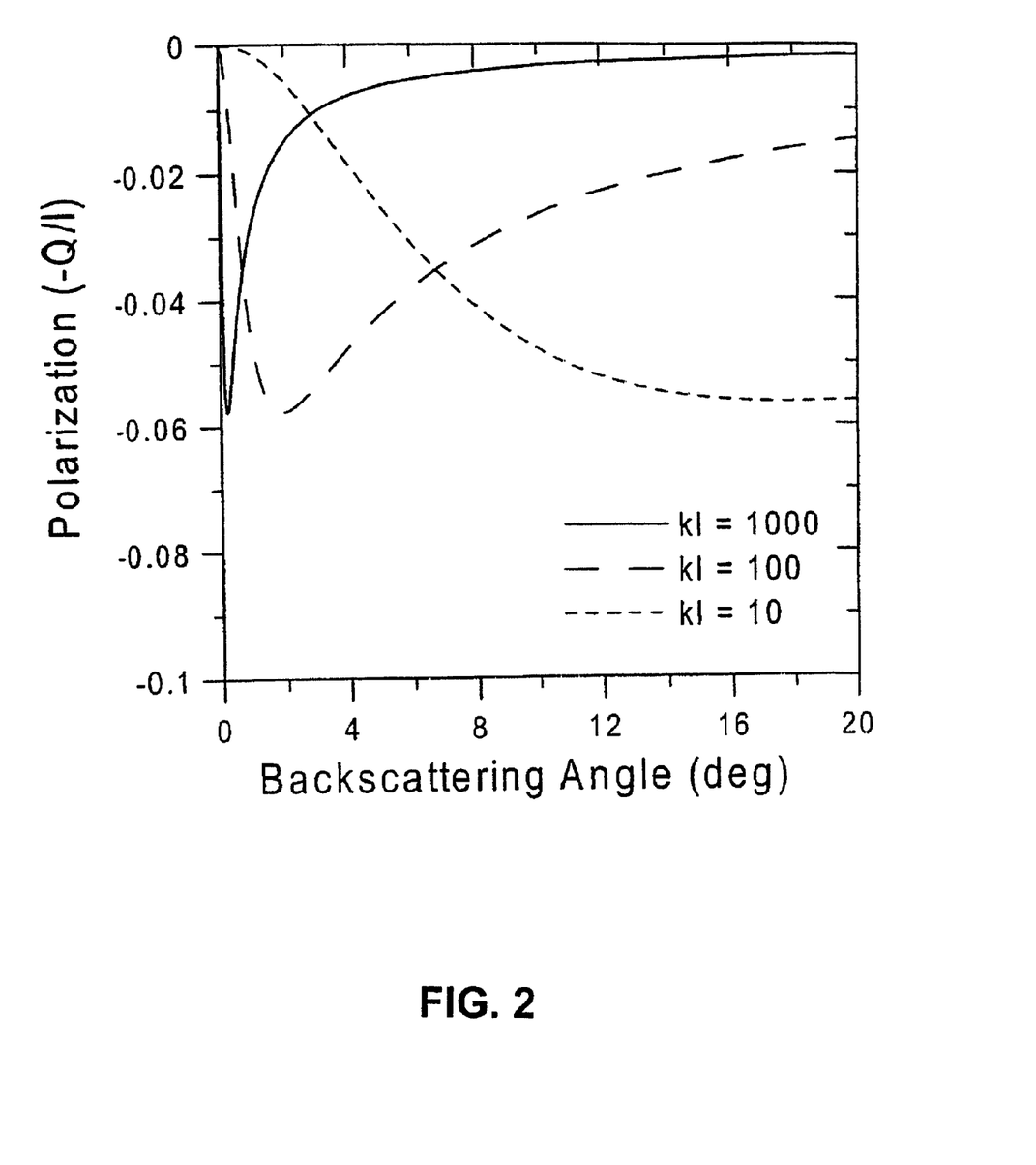
FIG. 2 is a graph depicting polarization of scattered light resulting from second-order ray tracing versus back-scattering angle from a cloud of small particles (dipoles) of FIG. 1 for three arbitrary values of kl.

FIG. 2 shows sample calculations for different spatial parameters kl=10, 100, 1000. Note that the shape of the polarization curve calculated from dipoles remains highly asymmetric. These results are consistent with the calculations of Mishchenko et al., who found that the angular profile of the polarization opposition effect only depends on the dimensionless parameter $q=kl\gamma$.

Figure 3:
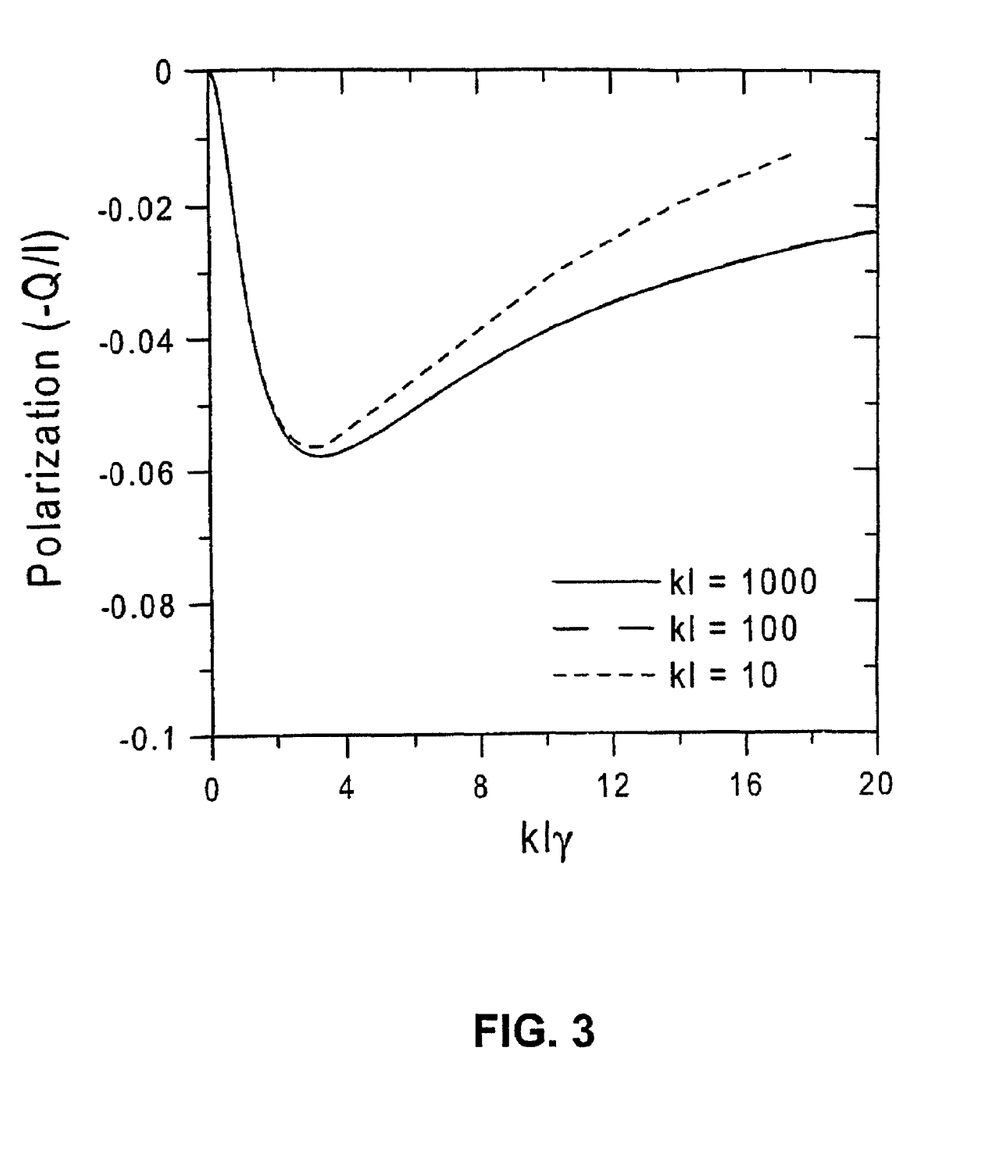
FIG. 3 is a graph of the curves of FIG. 2 plotted as a function of the dimensionless parameter $q=kl\gamma$.

FIG. 3 shows a plot of our model results as a function of this dimensionless parameter. Note that differences only appear in the curves when $q=kl\gamma$ approaches the wavelength (at which point the model breaks down because $\gamma$ is assumed to be small). The shape of this curve closely resembles that shown by Mishchenko et al., and the minima are also located at approximately the same position $q_{min} \sim 3.36$ in Mishchenko et al. and $q_{min} \sim 3.14$. Note that there is a factor of two difference in how the mean free path is defined in these works. The amplitude of the polarization is significantly larger in our model results because we do not include other orders of scattering.

Although these results amount to a verification of the rigorous results from a cloud of dipoles, they do have stronger implications, especially with regard to the branch of negative polarization. While the results of various ray-tracing programs would lead us to conclude that constructive interference of reciprocal rays is the mechanism for the negative polarization, the more accurate calculations from a cloud of dipoles could not produce this branch. Whether the negative branch is a result of the constructive interference of reciprocal rays or an artifact of the ray-tracing models remains open to debate. Since the physics in the model is adequate enough to reproduce the essential characteristics of the results from a cloud of dipoles, we are led to believe that it is also adequate to reproduce the essential characteristics from a cloud of surface facets, and that the symmetric negative polarization seen in the latter system is not an artifact and is due to constructive interference of reciprocal rays. One further implication of this is that if a system displays a symmetric branch, this branch is not the result of multiple scattering by dipoles.

Figure 4:
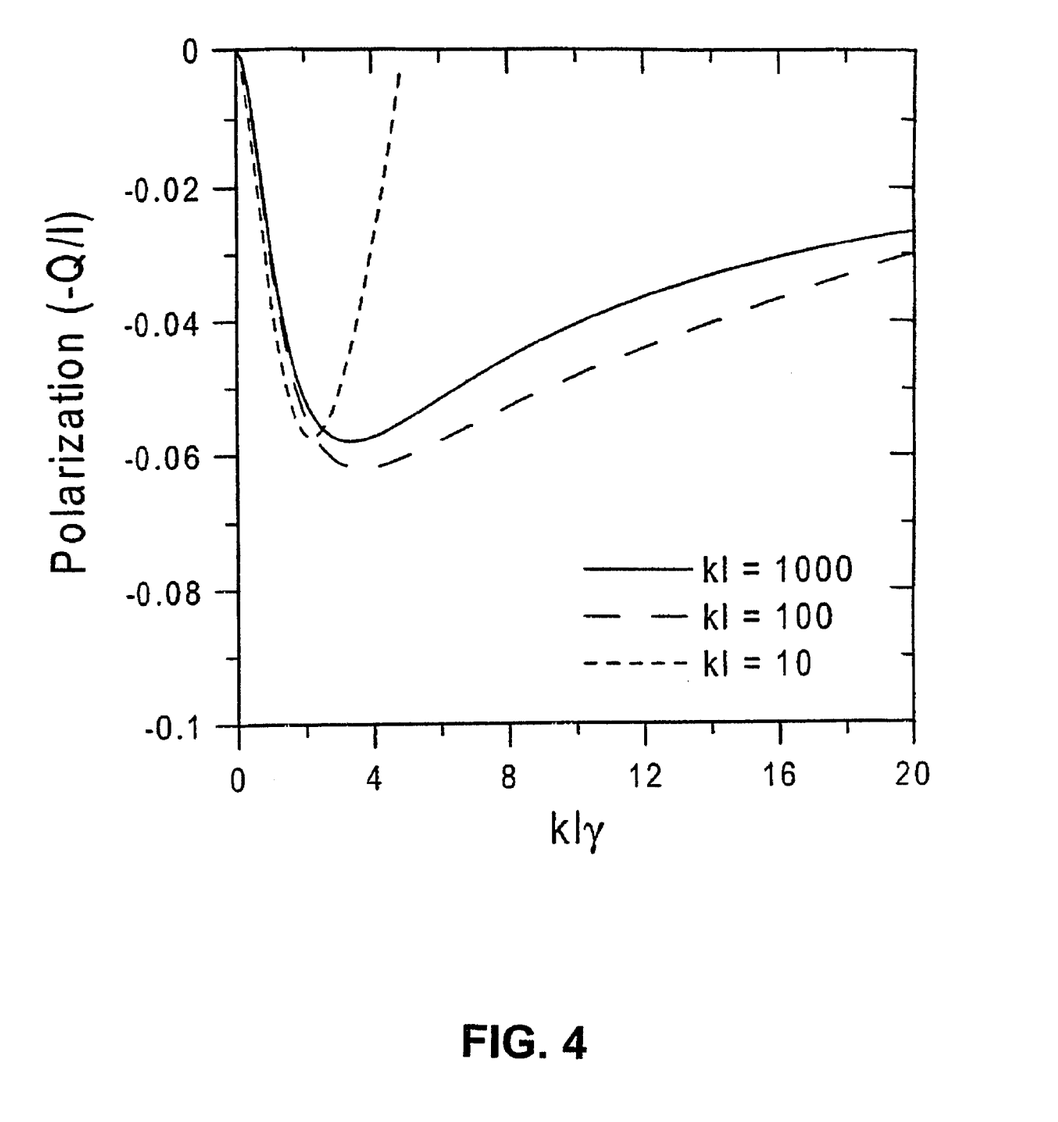
FIG. 4 is a graph depicting polarization state of scattered light resulting from second-order ray-tracing from a cloud of r=λ/10, m=1.55 spheres.

Finally, the model's versatility allows us to consider other scattering systems. Dipoles, for instance, can be replaced with spheres by substituting their scattering amplitude matrices in Eqn. 4. FIG. 4 shows sample polarization results when we consider spheres of finite size, in this case, $r=\lambda/10$, m=1.55 spheres. Even though the spheres would normally be considered quite small, just beyond the Rayleigh range, the polarization response is significantly different from Rayleigh spheres. The shapes of the curves now have a strong dependence on separation parameter kl. For relatively large kl, the polarization response is strongly asymmetric, as was seen in FIG. 3, but for smaller separation parameter (kl=10), the curve is now parabolically shaped.

Figure 5:
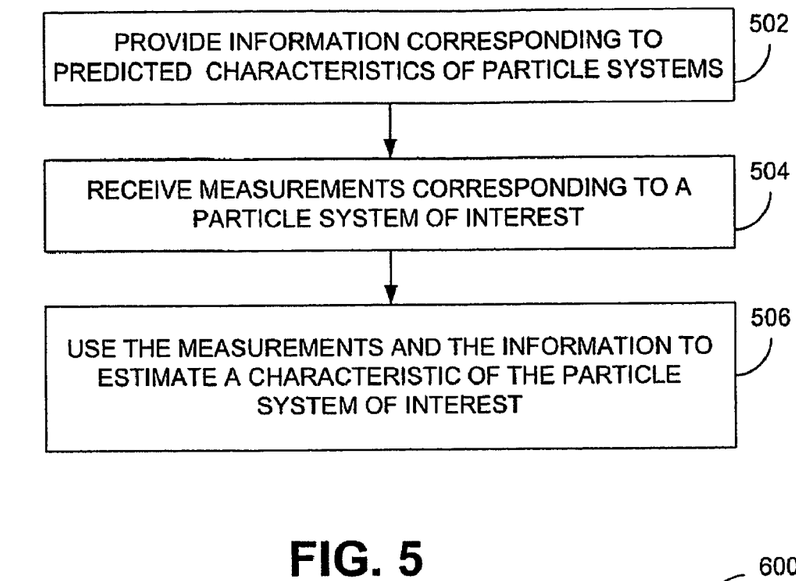
FIG. 5 is a flowchart depicting functionality of an embodiment of a system for analyzing particle systems.

Having thus described the model for predicting the second-order scattering, reference will now be made to FIGS. 5–8, which will be used to describe embodiments of systems and methods for analyzing particle systems. As shown in FIG. 5, which is a flowchart depicting functionality of an embodiment of a system for analyzing particle systems, the functionality (or method) may be construed as beginning at block 502, where information corresponding to predicted characteristics of particle systems is provided. By way of example, information can be obtained using the model described above with respect to particle systems exhibiting a range of parameters. The information could be stored in graphical form or as entries in a database, for example, so that the information can be accessed when needed. In block 504, measurements corresponding to a particle system of interest are received. For instance, a detector placed in position with respect to a particle system of interest, such as depicted in FIG. 1, can be used to acquire measurements. Specifically, the measurements can include values of $I_{TM}$ and $I_{TE}$ over a range of back-scattering angles. These measurements can be used to calculate polarization percentages $(I_{TE}-I_{TM}/I_{TE}+I_{TM})$ versus back-scattering angle. Then, in block 506, the measurements and the information are used to estimate a characteristic of the particle system of interest. In particular, the minimum values of the measured polarization of the particle system of interest can be correlated with the information obtained using the model.

Systems for analyzing particle systems can be implemented in software, firmware, hardware, or a combination thereof. When implemented in hardware, each of the systems can be implemented with any or a combination of various technologies. By way of example, the following technologies, which are each well known in the art, can be used: a discrete logic circuit(s) having logic gates for implementing logic functions upon data signals, an application specific integrated circuit (ASIC) having appropriate combinational logic gates, a programmable gate array(s) (PGA), and a field programmable gate array (FPGA).

When implemented in software, a system for analyzing particle systems typically is used in conjunction with a computer or processor-based device. An example computer that can be used to implement an embodiment of a system for analyzing particle systems is depicted in FIG. 6.

Figure 6:
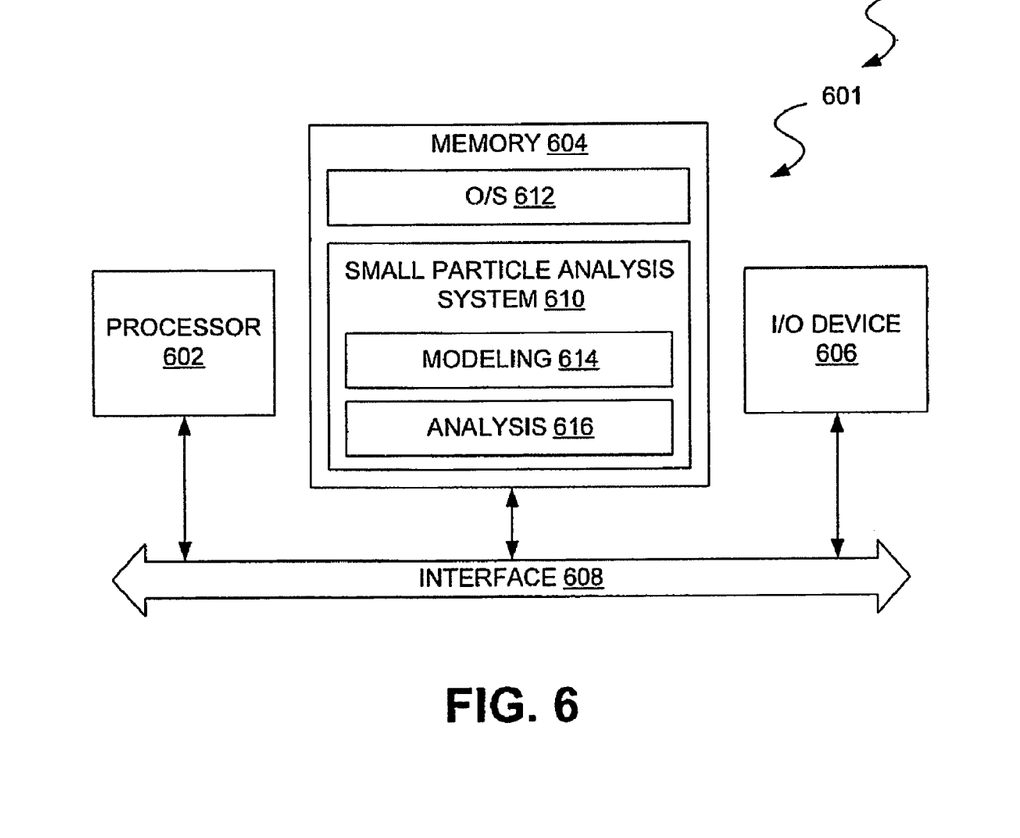
FIG. 6 is a schematic diagram depicting a computer or processor-based system that can be used to implement an embodiment of a small particle analysis system.

As shown in FIG. 6, an embodiment of a system for analyzing particle systems 600 includes a computer 601 that incorporates a processor 602, memory 604, and one or more input and/or output (I/O) devices 606 (or peripherals) that are communicatively coupled via a local interface 608. The software in memory 604 can include one or more separate programs, each of which comprises an ordered listing of executable instructions for implementing logical functions. In the example of FIG. 6, the software in the memory 604 includes a small particle analysis system 610 and an operating system (O/S) 612. Note, small particle analysis system 610 includes a modeling subsystem (module) 614 and an analysis subsystem (module) 616.

When small particle analysis system 610 is implemented in software, it should be noted that the system can be stored on any computer-readable medium for use by or in connection with any computer-related system or method. In the context of this document, a computer-readable medium is an electronic, magnetic, optical, or other physical device or means that can contain or store a computer program for use by or in connection with a computer-related system or method. Small particle analysis system 610 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Functionality of the embodiment of the small particle analysis system 610 of FIG. 6 will now be described with respect to the flowchart of FIG. 7. Note that the functions associated with the blocks of the flowchart of FIG. 7, or any of the other flowcharts of this disclosure, may occur out of the order in which they are depicted. In some embodiments, the functionality associated with multiple blocks could be executed substantially concurrently or sometimes in the reverse order.

Figure 7:
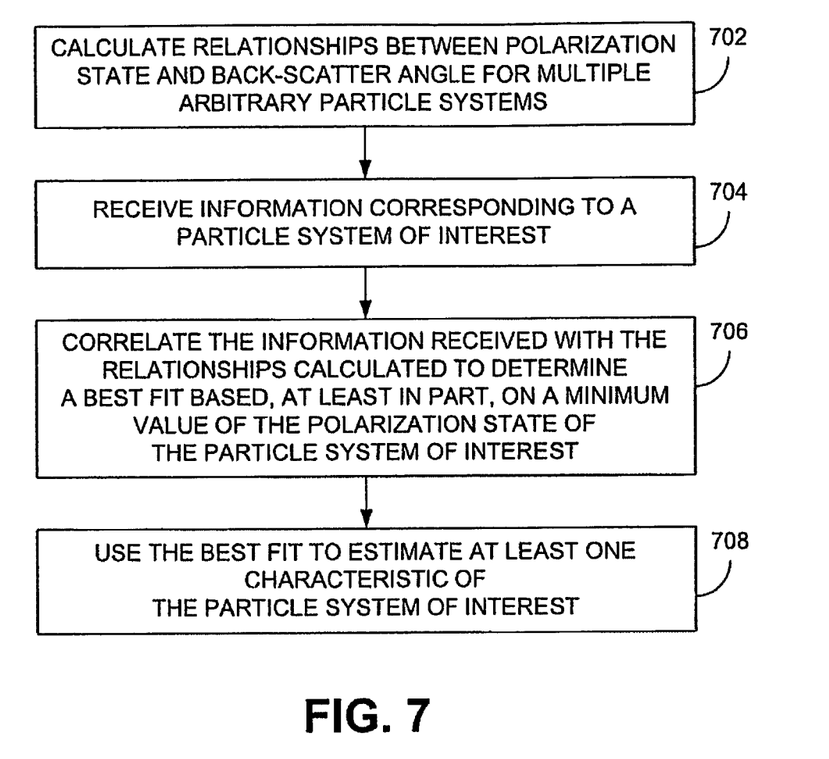
FIG. 7 is a flowchart depicting functionality of the embodiment of the small particle analysis system of FIG. 6.

As shown in FIG. 7, the functionality (or method) may be construed as beginning at block 702, where relationships between polarization state and back-scatter angle are calculated for multiple arbitrary particle systems. In block 704, information corresponding to a particle system of interest is received. In block 706, the information received is correlated with the relationships calculated to determine a best fit based, at least in part, on a minimum value of the polarization state of the particle system of interest. That is, the back-scattering angle at which the minimum polarization state occurs is compared to the back-scatter angles at which the minimum positions are predicted to occur for the arbitrary particle system to the model. In block 708, the best fit is used to estimate at least one characteristic of the particle system of interest.

In some embodiments, relationships between polarization state and back-scatter angle are calculated by a modeling subsystem, e.g., modeling subsystem 614, that implements the modeling theory described before. The functionality of such an embodiment will now be described with respect to the flowchart of FIG. 8.

Figure 8:
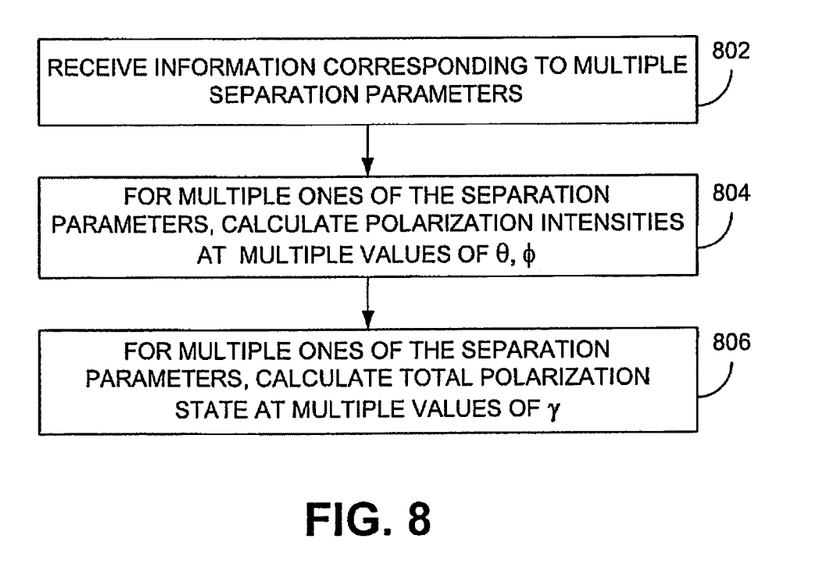
FIG. 8 is a flowchart depicting functionality of the embodiment of the prediction module of the small particle analysis system of FIG. 6.

As shown in FIG. 8, the functionality (or method) of an embodiment of a modeling subsystem may be construed as beginning at block 802, where information corresponding to multiple separation parameters is received. In block 804, polarization intensities at multiple values of $\theta, \phi$ are calculated for multiple ones of the separation parameters. In block 806, total polarization state at multiple values of $\gamma$ are calculated for multiple ones of the separation parameters. Once calculated, the values can be stored in a memory storage device, e.g., memory 604, and accessed as needed. Typically, an analysis system 616 accesses the values and correlates the values with information corresponding to a particle system of interest.

A dipole is a small scatterer (i.e., small compared to the wavelength of the light ray) and the model relates to the characterizations of small particles. Examples of possible applications include the detection of small amounts of carbon in asteroids (quantity and spacing); detecting the presence of nano-particle concentrations in material science and clean-room technology applications; detecting and observing chemistry processes and experiments; detecting and quantifying environmental and chemical pollutants; and measuring contaminants in air and liquid samples.

It should be emphasized that many variations and modifications may be made to the above-described embodiments. All such modifications and variations are intended to be included herein within the scope of this disclosure and protected by the following claims.

What is claimed is:

1. A method for analyzing particle systems using polarized scattered light, said method comprising the steps of:
   providing models of multiple particle systems of dipoles;
   performing ray-trace analysis with respect to the models over a range of scatter angles, the ray-trace analysis involving only use of second-order rays;
   receiving information corresponding to a particle system of interest; and
   predicting at least one characteristic of the particle system of interest using information generated during the ray-trace analysis.

2. The method of claim 1, wherein, in performing ray-trace analysis, constructive interference of the second-order rays is considered.

3. The method of claim 1, wherein, in performing ray-trace analysis, information corresponding to polarization state at near-back-scatter angles is generated for each of the models.

4. The method of claim 1, wherein providing models of multiple particle systems comprises the step of:
   providing a model for each of multiple values of a separation parameter (l) for a selected particle size.

5. The method of claim 1, wherein:
   the method additionally comprises the step of:
   providing a memory storage device; and
   the information generated during the ray-trace analysis is stored in the memory storage device.

6. The method of claim 5, wherein predicting at least one characteristic of the particle system of interest comprises the steps of:
   accessing the information stored in the memory storage device;
   comparing the information corresponding to the particle system of interest to the information accessed to determine which model most closely corresponds to the particle system of interest.

7. The method of claim 6, wherein, in comparing the information corresponding to the particle system of interest to the information accessed, the minimum values of polarization state versus back-scatter angles are compared.

8. The method of claim 1, wherein:
the method additionally comprises the step of:
detecting values of TM and TE at various back-scatter angles with respect to the particle system of interest; and
the information received corresponds to the values of TM and TE detected.

9. A method for analyzing particle systems using polarized scattered light, said method comprising the steps of:
calculating relationships between polarization states and back-scatter angles with respect to multiple arbitrary particle systems;
receiving information corresponding to a particle system of interest;
correlating the information received with the relationships calculated to determine a best fit based, at least in part, on a minimum value of the polarization state of the particle system of interest; and
using the best fit to estimate at least one characteristic of the particle system of interest.

10. The method of claim 9, wherein, in calculating relationships, at least one of the multiple arbitrary particle systems is a cloud of dipoles.

11. The method of claim 10, wherein the cloud of dipoles is randomly distributed.

12. A computer-readable medium having a computer program stored thereon, the computer program being executable to perform computer-implemented method steps, said method steps comprising:
receiving information corresponding to a model of a distributed system of dipoles;
generating information corresponding to polarization state and back-scatter angle of the model at multiple separation parameters (l) using second-order ray-trace analysis;
receiving information corresponding to a particle system of interest; and
predicting at least one characteristic of the particle system of interest using the information generated.

13. The computer-readable medium of claim 12, wherein the method step of generating information comprises the step of considering constructive interference of second-order rays.

14. The computer-readable medium of claim 12, wherein the method step of predicting at least one characteristic of the particle system of interest comprises the steps of:
comparing the information corresponding to the particle system of interest to the information generated; and
determining which separation parameter most closely corresponds to the particle system of interest based on the comparing step.

15. The computer-readable medium of claim 14, wherein the method step of comparing the information corresponding to the particle system of interest to the information generated, the minimum values of polarization state versus back-scatter angles are compared.

16. A computer-readable medium having a computer program stored thereon, the computer program being executable to perform computer-implemented method steps, said method steps comprising:
calculating relationships between polarization states and back-scatter angles with respect to multiple arbitrary particle systems;
receiving information corresponding to a particle system of interest;
correlating the information received with the relationships calculated to determine a best fit based, at least in part, on a minimum value of the polarization state of the particle system of interest; and
using the best fit to estimate at least one characteristic of the particle system of interest.

17. The computer-readable medium of claim 16, wherein, in calculating relationships, at least one of the multiple arbitrary particle systems is a cloud of dipoles.

18. The computer-readable medium of claim 16, wherein the cloud of dipoles is randomly distributed.

19. A system for analyzing a particle system using polarized scattered light comprises:
a model of multiple dipole particle systems, the model being configured to provide information corresponding to polarization state and back-scatter angle of the multiple dipole particle systems at multiple separation parameters (l) using second-order ray-trace analysis; and
a computer operative to access the model, the computer being further operative to:
receive information corresponding to a particle system of interest; and
predict at least one characteristic of the particle system of interest using the information provided by the model.

20. The system of claim 19, further comprising:
means for storing the model such that the model is accessible by the computer.

* * * * *